United States Patent [19]

Shaw

[11] 4,263,811
[45] Apr. 28, 1981

[54] ADHESION TEST INSTRUMENT

[75] Inventor: Robert B. Shaw, Houston, Tex.

[73] Assignee: Shell Oil Company, Houston, Tex.

[21] Appl. No.: 57,472

[22] Filed: Jul. 13, 1979

[51] Int. Cl.³ .............................................. G01N 3/08
[52] U.S. Cl. ....................................... 73/827; 73/15.6
[58] Field of Search ..................... 73/827, 150 A, 842, 73/15.6, 847, 848

[56] References Cited

U.S. PATENT DOCUMENTS

| | | | |
|---|---|---|---|
| 2,763,149 | 9/1956 | Long et al. | 73/15.6 |
| 3,214,971 | 11/1965 | Hammond Jr. | 73/150 A |
| 3,590,631 | 7/1971 | Gonze . | |

Primary Examiner—Jerry W. Myracle

[57] ABSTRACT

Method and apparatus for measuring the normal stress required to remove an adhering thermoplastic rod from a substrate. Tensile strength of a bond can be measured reproducibly under controlled conditions. The tip of a thermoplastic rod, machined to a cone, is lowered into contact with a heated substrate and melting of the rod is allowed to proceed to a steady-state condition. After a bond is formed, the force required to break the bond is measured. The method permits rapid simulation of the essential conditions present during bond formation between a mineral filler surface and a polymer matrix.

14 Claims, 6 Drawing Figures

HEAT PLATE

MELT POLYMER

COOL

TEST

ADHESION TEST INSTRUMENT

BACKGROUND OF THE INVENTION

This invention relates to a method and apparatus for measuring the tensile bond strength between one end of a polymer rod and a flat substrate.

In the search for suitable materials which will be competitive with metals in articles of manufacture that utilize molding techniques during one of the manufacturing stages, it is desirable to find a material which has a high modulus of elasticity, a high degree of toughness, and which is suitable for low cost injection molding processes. Two possible candidates are epoxy resin composites and thermoplastic or polymer composites. With epoxy resin composites, strong adhesion to a substrate is virtually assured, but in the area of thermoplastic or polymer composites, weak bonds are to be anticipated. Since thermoplastic composites may be developed much more cheaply than epoxy resin composites, it is desirable to qualitatively and quantitatively measure the pertinent parameters of the former.

Design of reinforced polymer composites requires knowledge of the strength of bond between a mineral filler surface and a polymer matrix. In prior art methods, this may be somewhat laboriously determined by testing the composites in their final use conditions. However, this is a time consuming process, unsuitable for screening a host of parameters affecting the adhesion process. It is desirable, therefore, to develop a testing method that would permit rapid simulation of the essential conditions present during bond formation in an actual composite, in a short period of time. This would have the advantage of enabling one to measure the tensile strength of a bond reproducibly under controlled conditions. Numerous areas of interest would benefit from such a method. For example, it may be desirable to screen certain surface-chemical agents which are reputed to have adhesion promoting properties but for which no adhesion test data is available for the system of interest, viz., a silicate mineral in a polypropylene matrix. Another application would be testing of microscopic polymer/filler dispersions, such as fine vermiculite flakes in a polycarbonate matrix. Other areas where methods of this nature would be particularly useful are the evaluation of surface preparation techniques and optimization of temperature-time aging treatments in polymer-inter layer systems.

SUMMARY OF THE INVENTION

According to the invention, a method and apparatus is provided for measuring the tensile bond strength of a bond formed by adhesion of a test member to a substrate.

The apparatus used to measure the tensile strength of the bond formed by the adhesion of the member to a substrate comprises a surface which is supported generally below the member, which surface is used for adhering the member thereto. Means for gripping the member is provided, as well as means for bringing the member and the surface into contact and means for separating the member from the surface. This last mentioned means for separating the member from the surface may be a part of the means for bringing the member and the surface into contact. Means for melting the member when it is brought into contact with the surface is provided in order to initiate bond formation. Means are provided for measuring the force required to break the bond formed between the member and the surface after sufficient cooling has occurred to form a bond. It is preferred to have the force measuring means connected in an operative manner to the means for separating the member from the surface, thereby providing a convenient way to measure the force, although the force-measuring means can be connected to the surface or its support means if desired.

A support may be provided for mounting the various components which comprise the apparatus of the invention, including the means for gripping the member, the means for supplying heat and the surface.

To provide reproducibility, it is particularly useful to provide means for restricting the member to a single degree of linear motion in a direction normal to the surface.

The method of the invention comprises the following steps: The member being tested is supported above the surface, and heat which is sufficient to melt the member is applied to the surface. To permit proper bond formation, the end of the member which is brought into contact with the surface should be tapered to a small cross-sectional area. After the tapered end is brought into contact with the surface, melting takes place as the member and the surface are brought closer together. Melting is allowed to progress to a steady state so that the cross-sectional area of the melted area, or melt, is less than the cross-sectional area of the test member. After a bond is formed by allowing the melt to cool, a force is exerted sufficient to break the bond. The magnitude of the force which is required to break the bond is a representation of bond strength. In bringing the member and the surface into contact, it is desirable for the purpose of enhancing the reproducibility of the method to restrict the member to motion in a direction perpendicular to the surface.

BRIEF DESCRIPTION OF THE DRAWINGS

Advantages of the invention will become apparent on reference to the following detailed description and accompanying drawings in which.

DESCRIPTION OF A PREFERRED EMBODIMENT

Figure 1:
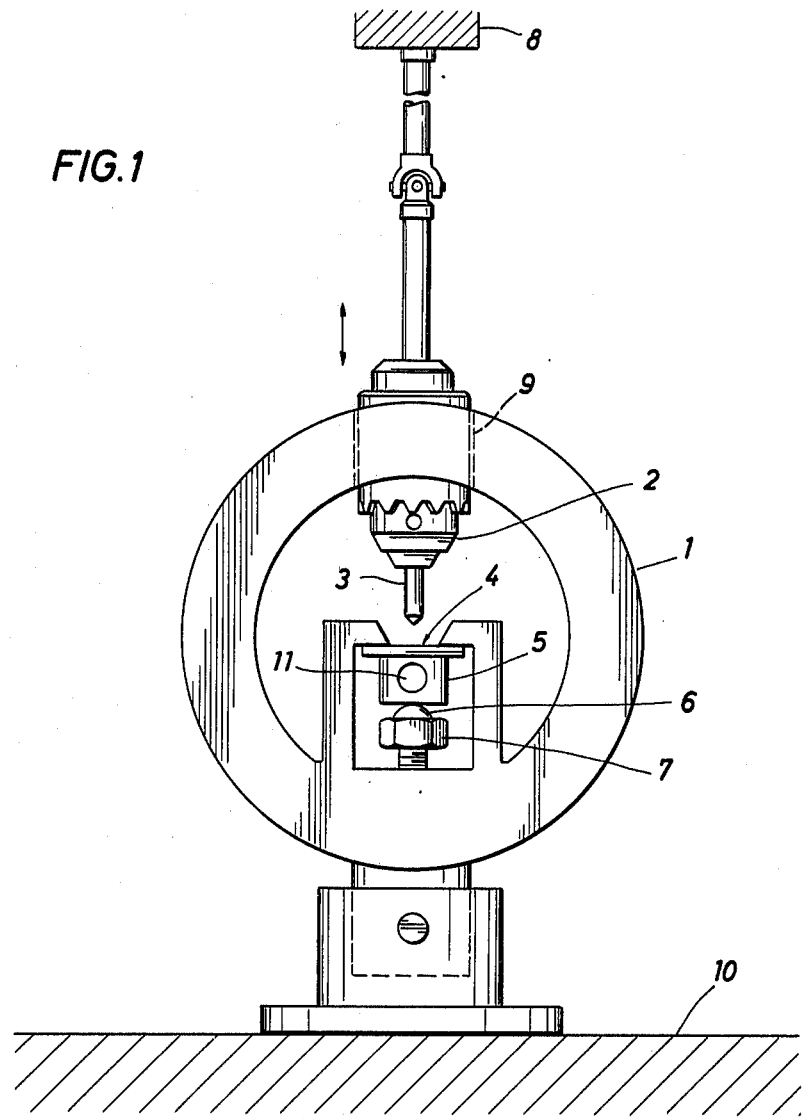
FIG. 1 illustratess an embodiment of the testing apparatus of the invention.

The principle of the invention will now be described with reference to FIG. 2. The essence of an adhesion test is that a tensile force is applied to a bonded configuration and increased until mechanical failure takes place. Where this failure takes place, the force is measured and a mode of failure identified by observing such things as fracture appearance characteristics. It is desirable to simplify mechanical design so that as few variables as possible affect interpretation of results. The principle of the method of the invention is to form an adhesive bond between the end of a thermoplastic rod 21 and a plate 22, over a circular area $A_o$ (indicated by arrows 25 of FIG. 2(d)). Thereafter, while maintaining alignment of rod 21 perpendicular to plate 22, an axial load P is slowly increased in a direction away from plate 22 until normal failure occurs. Tensile stress $P/A_o$ provides a measure of bond tensile strength.

For reasons which have been briefly mentioned and which will now be fully explained with reference to FIG. 1, it is necessary for accuracy and repeatability of the test method to taper the tip of the test member or rod.

If the member has a generally cylindrical shape, the end may take the form of a cone or a frustum of a cone. The end of a member of another shape could likewise have a conical shape or a pyramidal or a tetrahedral shape. This shaping may be accomplished by any method, for instance by machining or molding. It has been found especially useful to utilize a rod whose tip has been machined or shaped to a 90° cone.

If the tip of the rod has a cross section equal to that of the rod itself, it is difficult to prevent entrapment of microscopically small air bubbles at the bond interface. Tapering of the end improves the bond layer formed by preventing the entrapment of these small air bubbles in the bond interface. In addition, when a rod of uniform cross section is brought into contact with the hot substrate, such as plate 4, heat conduction processes tend to create a droplet whose diameter is greater than the initial rod diameter. In other words, the melting process geometry is difficult to control. A third reason for using a coned tip is that the bond interface of plate 4 and the thermoplastic member constitute a series-mechanical arrangement. Where a droplet of greater diameter exists at the interface of plate 4 and a rod of uniform cross section, the yield stress will decrease in a direction away from the plate. The rod would tend to fail at a location some distance from the bond interface.

By using a tapered or coned rod tip, these problems may be eliminated. The coned tip tends to melt progressively when lowered into contact with the plate, without entrapment of air bubbles. The heat flow is more rapid up the axis of a rod with a coned tip compared to one of uniform cross section because the mass of a cone-tipped rod above the melt is larger for a given contact area than a rod of uniform cross section. When tensile load is applied, the average stress is highest where the area is smallest, at the bond interface. Thus, the bond interface and the thermoplastic material immediately adjacent the interface experience virtually the same stress distribution. Failure may occur by de-adhesion or de-cohesion but geometry does not favor one over the other since both experience the same stress, which is a maximum in the region of interest.

The surface which is brought into contact with the rod may take any of several forms, as long as it is non-meltable at the melting temperature of the rod. Although a flat glass plate is referred to in this description, any shape will suffice if the surface area brought into contact with the coned-tip is flat. The means for melting the rod may be any heat source which is capable of supplying the requisite amount of heat, and may be located adjacent to the surface. However, it may be equally efficient to utilize a plate with an electrically conductive and resistive element placed therein such that internal heating of the plate would occur by application of electric current to the element.

Bringing the rod into contact and separating it from the surface may be accomplished equally well by moving the member into contact with a stationary surface, by moving the surface into contact with the stationary member, or by simultaneously moving the member and the surface into contact with each other.

Referring now to FIG. 1, a representation of the test apparatus appears wherein a short length of a thermoplastic test member 3 is tightly held in grip 2. Grip 2 may be limited to only one degree of linear motion in the direction indicated by the double arrow, by providing a sliding fit in a cylindrical hole 9 in rigid support frame 1. Grip 2 is operatively attached to load cell 8, which is fixed rigidly in place, and support frame 1 is attached to cross head 10. Cross head 10 may be raised or lowered in a controlled manner to move the surface of glass plate 4 toward or away from member 3. Directly below meltable member 3, plate 4 is held in place by heater 5, spring 6 and adjustable nut 7. Heater 5 may comprise a 50 watt electric cartridge heater inserted in aperture 11 of a heating block.

Cross head 10 and load cell 8 may comprise a commercially available tensile testing machine such as one manufactured by Instron Corporation.

Referring to FIG. 2 in combination with FIG. 1, a typical test cycle is illustrated. With glass plate 22 installed between frame 1 and heater 5 of FIG. 1, and a suitable rod 21 mounted in grip 2 of FIG. 1, frame 1 is attached to cross head 10. Grip 2 is then suspended from fixed load cell 8. Grip 2 is slidably fitted in cylindrical hole 9 of frame 1, and conical tip 23 of rod 21 of FIG. 2 is brought almost into contact with plate 22 as illustrated in Step (a) of FIG. 2. Glass plate 22 is heated to a suitable temperature above the melting point of rod 21 by heater 5. Of course, heating of plate 22 may also take place after tip 23 is in contact therewith. In Step (b) of FIG. 2, tip 23 is pressed against now-heated surface 22, and the thermoplastic meniscus is allowed to form at interface 24. Cross head 10 is only raised a sufficient amount to provide an ample melted area at interface 24 for a proper bond, since it is important to maintain the cross-sectional area of the meniscus less than the cross-sectional area of the rod. The conical shape of tip 23 permits a stable geometric form to be retained by molten thermoplastic in the steady state. Cooling then is allowed to occur in Step (c) of FIG. 2 which may be facilitated by disabling heater 5, such as by removing the 50 watt cartridge heater from aperture 11 of FIG. 1, and inserting into the aperture a solid copper rod which has been pre-cooled to some point below ambient temperature, for instance, 0° C. Other methods of cooling will be equally successful, such as application of a coolant or forced air. When the temperature becomes unifrom, cross head 10 is lowered at a slow rate, such as 0.002" to 0.005"/minute, and tensile load versus time is recorded. After failure has occurred, illustrated by Step (d) of FIG. 2, plate 22 is removed and the cross-sectional area of area 25 is determined. Bond strength may be determined by conventional force equations, as previously mentioned. Plate 22 may be examined for indications whether the fracture occurred in the plate 22, along interface 24, or in rod 21.

Figure 3:
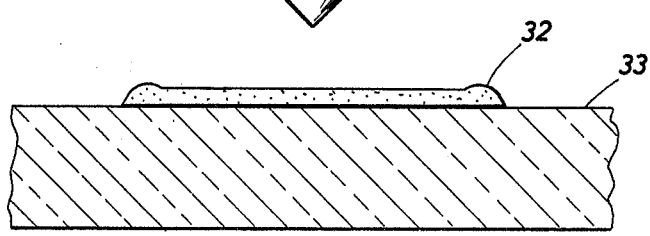
FIG. 3 represents a test using the apparatus of the invention for measuring the adhesive strength of filler particles in a matrix.
Figure 2A:
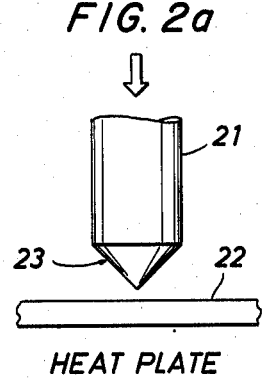
FIG. 2a–2d represent the sequence of operations performed in carrying out a typical test by the method of the invention.
Figure 2B:
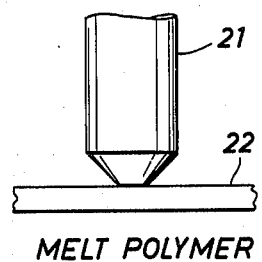
Figure 2C:
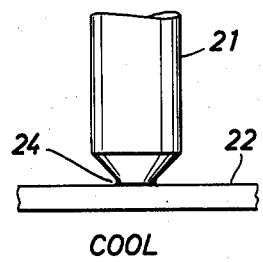
Figure 2D:
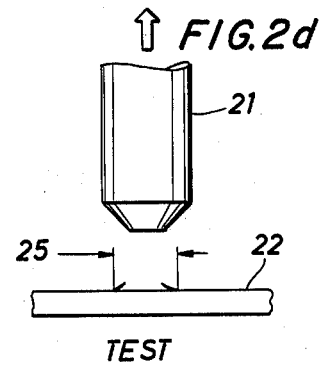

With the method and apparatus of the invention, one may study the effects of certain chemical pre-treatments on bond strength by utilizing the invention. A chemical pre-treatment containing filler particles may be thought of as forming one or more thin parallel layers of the filler particle on the test surface. These thin layers may range from a molecular film to a coating several microns in thickness. This "thin layer concept" may be applied in the field of reinforced polymer composites, where it is important to determine such things as the cohesive strength within a reinforcing filler particle, adhesive strength of the filler particles to the polymer matrix and the state of interpenetration of particle agglomerates by the polymer during processing. Referring to FIG. 3, a dilute suspension of filler particles in a solvent containing a polymer of interest is cast on plate 33 to form a thin film 32. The solvent is then extracted by vacuum annealing. If the particles are in the form of flakes or needles, they will align parallel to plate 33. The rod used in the test will be made of the same polymer that has been left on plate 33 after the solvent is removed. A bond is formed by lowering the tip of rod 31 into contact with heated plate 33 and cooling, as previously described with reference to FIG. 2. The molecules of polymer from the plate and the rod commingle and the filler particles are trapped in close proximity to the surface of plate 33. The strength measured by the method previously described is then a measure of strength of the composite of the polymer and the filler particles where failure occurs within the composite. As the filler-polymer adhesion is increased, failure may occur in the polymer rod. This latter point of failure then defines a lower limit to composite strength. Of course failure may also occur at the plate surface, or within the plate itself, either of which would give, at least, a lower limit to composite strength.

To insure a proper bond at the surface of a glass plate when utilizing the invention, it is especially useful to treat the plate to remove all contaminants. The glass plate is first rubbed with a wetted metallurgical polishing cloth using levigated alumina as a fine abrasive. This removes a thin layer of glass, but still retains overall flatness and a scratch-free condition. Next, the surface is flushed with a fluid such as air or water to dispel any alumina particles still adhering to the surface. As a final step, the plate is flushed with absolute ethanol and dried. This process provides a glass plate particularly suitable for the testing method and apparatus of the invention.

It will be understood that various modifications of this test method and apparatus may occur to those skilled in the art, e.g., the rod may be twisted in torsion rather than pulled in tension, and it is intended that this invention be limited only by the scope of the appended claims.

What is claimed is:

1. Apparatus for measuring the tensile strength of a bond caused by the adhesion of a tapered end of a test member to a surface, comprising:
    a surface, supported generally below a test member, for adhering said member thereto;
    means for gripping said member;
    means for bringing a tapered end of said member and said surface into contact;
    means for melting said tapered end when said member is in contact with said surface so that the cross-sectional area of the melted area is less than that of said member;
    means for separating said member from said surface; and
    means for measuring the force required to separate said member from said surface after a bond has formed therebetween.

2. Apparatus according to claim 1, wherein said separating means is a part of said means for bringing said member and said surface into contact.

3. Apparatus according to claim 2 wherein said means for separating and said means for bringing into contact are restricted to one degree of linear motion in a direction normal to said surface.

4. Apparatus according to claim 1, wherein said melting means is a heating means located adjacent said surface.

5. Apparatus according to claim 1, wherein said force measuring means is operatively connected to said separating means.

6. Apparatus according to claim 1, wherein said surface, said gripping means, and said melting means are mounted on a support frame.

7. Apparatus according to claim 1, wherein said surface is a flat plate of glass.

8. Apparatus according to claim 7, wherein said melting means comprises an electric resistance element contained in said glass plate.

9. Method of measuring the tensile strength of a bond formed by the adhesion of the tapered end of a test member to a surface, comprising the steps of:
    supporting said member above said surface;
    bringing said member and said surface into contact;
    melting the tapered end of said test member by heat applied to said surface;
    allowing the melting of said member to progress to a steady state such that the meniscus formed by said melting has a smaller cross-sectional area than said member;
    allowing said surface to cool such that a bond is formed between said surface and said member;
    applying a tensile force to said member sufficient to break said bond; and,
    determining the tensile strength of said bond.

10. Method according to claim 9, wherein said member is restricted to motion in a direction normal to said surface.

11. Method according to claim 9, wherein the tip of said member is shaped in a cone.

12. Method according to claim 9, wherein said surface is cleaned prior to said measuring by:
    rubbing said surface with a metallurgical polishing cloth using a fine abrasive;
    flushing said rubbed surface with fluid to dispel any particles of said abrasive;
    flusing said surface with absolute ethanol; and,
    drying said surface.

13. Method according to claim 9, wherein the tip of said member is shaped in 90° cone.

14. Method of measuring the torsional strength of a bond formed by the adhesion of the tapered end of a test member to a surface, comprising the steps of:
    supporting said member above said surface;
    bringing said member and said surface into contact;
    melting the tapered end of said test member by heat applied to said surface;
    allowing the melting of said member to progress to a steady state such that the meniscus formed by said melting has a smaller cross-sectional area than said member;
    allowing said surface to cool such that a bond is formed between said surface and said member;
    applying a torsional force to said member sufficient to break said bond; and
    determining the torsional strength of said bond.

* * * * *